US008518872B2

(12) United States Patent
Silverman

(10) Patent No.: US 8,518,872 B2
(45) Date of Patent: Aug. 27, 2013

(54) METHODS OF USING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID IN COMBINATION THERAPY

(75) Inventor: Jeffrey A. Silverman, Burlingame, CA (US)

(73) Assignee: Sunesis Pharmaceuticals, Inc., South San Francisco, CA (US)

(*) Notice: Subject to any disclaimer, the term of this patent is extended or adjusted under 35 U.S.C. 154(b) by 10 days.

(21) Appl. No.: 12/739,139

(22) PCT Filed: Oct. 21, 2008

(86) PCT No.: PCT/US2008/011960
§ 371 (c)(1),
(2), (4) Date: Aug. 9, 2010

(87) PCT Pub. No.: WO2009/054935
PCT Pub. Date: Apr. 30, 2009

(65) Prior Publication Data
US 2010/0297142 A1    Nov. 25, 2010

Related U.S. Application Data

(60) Provisional application No. 60/981,766, filed on Oct. 22, 2007.

(51) Int. Cl.
*A61F 2/00* (2006.01)
*A61K 38/00* (2006.01)

(52) U.S. Cl.
USPC .............................. 514/2; 424/422

(58) Field of Classification Search
None
See application file for complete search history.

(56) References Cited

U.S. PATENT DOCUMENTS

| 4,261,989 | A | 4/1981 | Sasaki et al. |
| 5,134,127 | A | 7/1992 | Stella et al. |
| 5,817,669 | A | 10/1998 | Tomita et al. |
| 6,171,857 | B1 | 1/2001 | Hendrickson |
| 6,291,643 | B1 | 9/2001 | Zou et al. |
| 6,570,002 | B1 | 5/2003 | Hardwick et al. |
| 6,641,810 | B2 | 11/2003 | Gold |
| 6,670,144 | B1 | 12/2003 | Craig et al. |
| 6,696,483 | B2 | 2/2004 | Singh |
| 7,211,562 | B2 | 5/2007 | Rosen et a |
| 7,869,577 | B2 | 1/2011 | Arnison |
| 7,968,565 | B2 | 6/2011 | Arkin et al. |
| 7,989,468 | B2 | 8/2011 | Adelman et al. |
| 8,124,773 | B2 | 2/2012 | Adelman et al. |
| 2003/0165887 | A1 | 9/2003 | Reed |
| 2005/0203120 | A1 | 9/2005 | Adelman et al. |
| 2005/0215583 | A1 | 9/2005 | Arkin et al. |
| 2006/0025437 | A1 | 2/2006 | Adelman et al. |
| 2008/0063642 | A1 | 3/2008 | Adelman et al. |
| 2009/0263393 | A1 | 10/2009 | Adelman et al. |
| 2010/0029708 | A1 | 2/2010 | Adelman et al. |
| 2010/0048609 | A1 | 2/2010 | Jacobs |
| 2010/0203162 | A1 | 8/2010 | Sudhakar et al. |
| 2011/0008371 | A1 | 1/2011 | Michelson |
| 2011/0082169 | A1 | 4/2011 | Sudhakar et al. |

FOREIGN PATENT DOCUMENTS

| JP | 62033176 A | 2/1987 |
| JP | 9221424 A | 8/1997 |
| JP | 11349565 A | 6/1998 |
| JP | 2003127542 A | 5/2003 |
| WO | WO2002020500 A1 | 3/2002 |
| WO | WO 2002036171 A1 | 5/2002 |
| WO | WO2004085418 A1 | 10/2004 |
| WO | WO2005/089756 | * 9/2005 |
| WO | WO2005089756 A1 | 9/2005 |
| WO | WO2005089757 A1 | 9/2005 |
| WO | WO2007/028171 | * 3/2007 |
| WO | WO2007028171 A1 | 3/2007 |
| WO | WO2010099526 A1 | 2/2010 |

OTHER PUBLICATIONS

Anderson et al. in Journal of Clinical Oncology (Abstract) 12(9), 1821-1826 (1994).*
Abratt et al. in Journal of Clinical Oncology (Abstract) 12(8), 1535-1540 (1994).*
Sato et al. in Abstract 11th NCI-EOARTC-AACR symposium on new drugs in cancer therapy, Nov. 7-10, 2000.*
Arbitrario, et al. "SNS-595 A Novel S-Phase Active Cytotoxic Acts Synergistically With Cytarabine to Reduce Bone Marrow Cellularity and Circulating Neutrophils," American Society of Hematology Conference, 2006.
Burris, et al. "SNS-595: Preliminary results of 2 phase 2 second line studies in lung cancer," European J. of Cancer, 2007, 5, 371-372.
Chiba, et al. "Practical Synthesis of AG-7352, Optically Active New Antitumor Agent," Abstract, 218.sup.th ACS National Meeting, Aug. 22-26, 1999.
Evanchik, et al. "Non-Clinical Admet, PK, and Biological Activity of Sns-595, a Novel Cell Cycle Inhibitory.Antineoplastic Agent," Drug metabolism reviews, Marcel Dekker, New York, NY, US, vol. 36, No. SUPPL1, Aug. 2004, p. 103. XP008073741.
Goodman & Giilman, "The Pharmacological Basics of Therapeutics," McGraw-Hill Medical Publishing Division, Tenth Ed., 2001, pp. 1404-1411.
Jacob, Leonard S., "National Medical Series of Independent Study: PHarmacology," Fourth Ed., 1996, Chapter 11, pp. 253-274.
Kashimoto, et al. Database BIOSIS Accession No. 2001:366681, "Antitumor Activity of a Novel Quinolone Analog AG-7352 in Human Xenograft Models of Leukemia or Drug-Resistant Tumors and in Experimental Metastatic Tumor Model", Proceedings of the Annual Meeting of the American Association for Cancer Research, New York, NY, 2001, vol. 42, p. 102—Abstract 553.
Lawrence, et al. "SNS-595, a Novel S-Phase Active Cytotoxic, Demonstrates Pharmacologic Properties Appropriate for the Treatment of Advanced Hematologiv Malignancies," Blood, 2005, vol. 106, No. 11. Part 2, p. 2378.

(Continued)

*Primary Examiner* — Dennis Heyer
(74) *Attorney, Agent, or Firm* — Jones Day

(57) ABSTRACT

Methods of treating, preventing or managing cancers are disclosed. The methods encompass the administration of SNS-595 in combination with a second active agent. In certain embodiments, the method of treatment comprise administering SNS-595 in combination with cisplatin, carboplatin, gemcitabine or a combination thereof.

15 Claims, 12 Drawing Sheets

(56) References Cited

OTHER PUBLICATIONS

Figure 1:
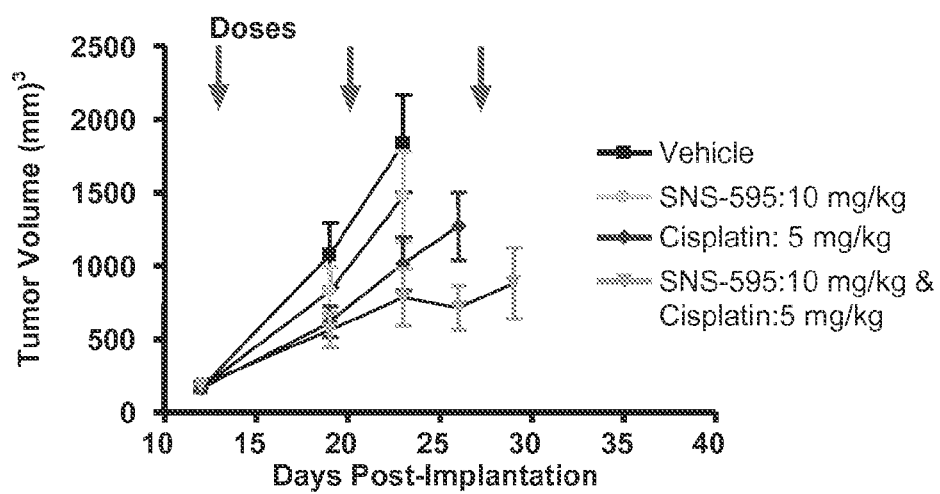

Lawrence, et al. "SNS-595, A Novel S-Phase Active Cytotoxic, Exhibits Potent in Vitro and in Vivo Activities, and has the Potential for Treating Advanced Hemotoloic Malignacies," Proceedings of the Annual Meeting of the AMerican Association for Cancer Research, New York, NY, 2006, vol. 47, p. 1110.

The Merck Manual, 1999, Chapters 142-144, p. 973-995.

Nakano, et al. "Antitumor Activity of a Novel Quinolone DNA Topoisomerase II Inhibitor AG-7352," Proceedings of the Annual Meeting of the American Association for Cancer Research, New York, NY, 1999, vol. 40, p. 115—Abstract 767.

Cleton F.J., "Chemotherapy: general aspects," Oxford Textbook of Oncology, 1995, vol. 1, pp. 445-453.

Sato, et al. "In Vivo Antitumor Activity of a Novel Quinolone Analogue AG-7352 Against a Borad-Spectrum of Cancers and Drug-Resistant Human Cancers," 2001, Abstract, 11th NCI-EOARTC-AACR symposium on new drugs in cancer therapy.

Stockett, et al. "Voreloxin is synergistic in in vitro combination with cyatarabine and additive in combination with azacitidine, decitabine and clofarabine," Poster presentation at EORTC. 2009.

Therasse, et al. "New Guidelines to Evaluate the Response to Treatment in Solid Tumors," Journal of the national Cancer Institute, 2000, vol. 92, No. 3.

Thirion, et al. "Interest of investigating p53 status in breast cancer by four different methods," Oncology Report, 2002, vol. 9, No. 6, pp. 1167-1172.

Tomita, et al. Database CAPLUS Accession No: 1999:92763, "Synthesis and Antitumor activity of Novel 7-Substituted 1, 4-dihydro-4-oxo-1-2(2-thiazolyl)-1,8-naphthyridine-3-carobxylic Acids," Abstracts of Papers American Chemical Society, 1999, vol. 217, No. 1-2, p. MEDI 249.

Tomita, et al. "Synthesis and Structure-Activity Relationships of Novel 7-Substituted 1.4-Dihydro-4-oxo-1-(2-thiazolyI)-1,8-naphthyridine-3-carboxylic Acids as Antitumor Agents, Part 1," J. Med. Chem., 2002, vol. 45, pp. 5564-5575.

Tsuzuki, et al. "Process Research of a Novel Quinolone Antitumor Agent, AG-7352," English Abstract, The Japanese Society for Process Chemistry, Summer Symposium, 2004.

Tsuzuki, et al. "Synthesis and Structure—Activity Relationships of 3-Substitued 1, 4-Dihydro-4-Oxo-1-(2-Thiazolyl)-1, 8-Naphthridines as Novel Antitumor Agents," Bioorganic & Medicinal Chem. Letters, 2004, vol. 14, pp. 3189-3193.

Tsuzuki, et al. "Synthesis of Optically Active Amine at C-7 Position of New Antitumor Agent AG-7352," Abstract, Molecular Chirality Conference, 1999.

Tsuzuki, et al. "Synthesis and Structure-Activity Relationships of Novel 7-Substituted 1,4-Dihydro-4-oxo-1-(2-thiazolyl)-1,8-naphthyridine-3-carboxylic Acids as Antitumor Agents, Part 2," J. Med. Chem., 2004, 2097-2109, vol. 47.

Tsuzuki et al. "Practical Synthesis of (3S,4S)-3-Methoxy-4-Methylaminopyrrolidine," Tet. Asym., 2001, 2989-2997, vol. 12.

Tsuzuki et al. "Efficient stereospecific synthesis of (S,S)-3-methozy-4-methylaminopyrrolidine," Tet. Asym., 2001,1793-1799, vol. 12.

Wright, et al. "SNS-595 Has Synergistic Activity in Vitro with DNA Damaging Agents and Antimetabolites," Proceedings of the Annual Meeting of the American Association for Cancer Research, New York, NY, 2006, vol. 47, p. 504.

Ohta et al. "Antitumor mechanism of a novel quinolone analogue AG-7352," 58th General Meeting of Japanese Cancer Association, 1999, p. 685 (Ref. No. 2297).

English language abstract of JP2003127542.

English language abstract of JP6233176.

English language abstract of JP9221424.

English language translation of JP11349565.

Goodman and Gilman's The Pharmacological Basis of Therapeutics, 10th ed., p. 54-56 (2001).

Kumer et al., AACR-NCI-EORTC International Conference on Molecular Targets, 2007.

Bonomi et al., J. Clin. Oncol., 7:1602-1613 (1989).

Anderson et al., Journal of Clinical Oncology, 12 (9), 1821-1826, (1994).

* cited by examiner

METHODS OF USING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID IN COMBINATION THERAPY

This application is a National stage under 35 U.S.C. §365 (c) of International Application No. PCT/US2008/011960, filed Oct. 21, 2008, which claims the benefit of priority of U.S. provisional application No. 60/981,766, filed Oct. 22, 2007, the contents of which are hereby incorporated by reference in their entireties.

1. FIELD

Provided herein are specific dosing regimens for treating, preventing or managing cancers with certain amounts of enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid in combination with certain amounts of a second anti-cancer agent or a combination of second agents. In certain embodiments, the methods encompass treating, preventing or managing solid tumors. It should be noted that the combinations or cocktails encompass simultaneous as well as sequential administration.

In one embodiment, the combination therapy comprises administering a certain amount of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, or a pharmaceutically acceptable salt, solvate or hydrate thereof and a certain amount of one or more second agent selected from carboplatin, cisplatin, and gemcitabine administered in particular cycles for specific cancers.

2. BACKGROUND

SNS-595 is chemically named (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, and has the following structure:

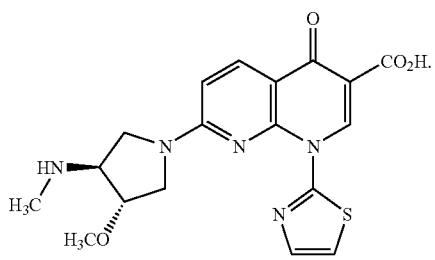 [SMILES: CN[C@H]1CN(c2ccc3c(=O)c(C(=O)O)cn(-c4nccs4)c3n2)C[C@@H]1OC]

SNS-595 is known for its anti-tumor activity. Treatment of the following cancers with SNS-595 has been proposed in the literature: bladder cancer, breast cancer, cervical cancer, colon cancer, esophageal cancer, head and neck cancer, liver cancer, lung cancer, melanoma, myeloma, neuroblastoma (i.e., CNS cancer), ovarian cancer, pancreatic cancer, prostate cancer, renal cancer, sarcoma, skin cancer, stomach cancer, testicular cancer, thyroid cancer, hematological cancer and uterine cancer. Various dosing regimens have been reported, for example, see, U.S. Patent Application Pub. Nos. 2005-0203120; 2005-0215583, 2006-0025437, and 2008-0063642 and International Publication No. WO 2007/028171, all of which are incorporated herein by reference in their entirety.

There continues to be a need for safe and effective dosages and dosing regimens for administering SNS-595 in treating, preventing and managing various cancers

3. SUMMARY

Provided herein are methods of treating, preventing or managing cancers, including, but not limited to bladder cancer, breast cancer, cervical cancer, colon cancer (including colorectal cancer), esophageal cancer, head and neck cancer, liver cancer, lung cancer (both small cell and non-small cell), melanoma, myeloma, neuroblastoma (i.e., CNS cancer), ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer. The cancer can be relapsed, refractory and/or resistant to conventional therapy.

The methods comprise administering to a subject a therapeutically or prophylactically effective amount of SNS-595, or a pharmaceutically acceptable salt, solvate or hydrate thereof thereof in combination with a second agent. In one embodiment, the second agent is selected from the group consisting of carboplatin, cisplatin, gemcitabine, and combinations thereof.

In one embodiment, the combination therapy comprises administering SNS-595, or a pharmaceutically acceptable salt, solvate or hydrate thereof thereof and carboplatin. In one embodiment, the combination therapy comprises administering SNS-595, or a pharmaceutically acceptable salt, solvate or hydrate thereof thereof and cisplatin.

In one embodiment, the combination therapy comprises administering SNS-595, or a pharmaceutically acceptable salt, solvate or hydrate thereof thereof and gemcitabine. Also provided are dosing regimens, dosing schedules and methods of using SNS-595, or a pharmaceutically acceptable salt, solvate or hydrate thereof thereof in combination with the second agents.

In one embodiment, the methods provided include the administration of SNS-595, or a pharmaceutically acceptable salt, solvate or hydrate thereof thereof in combination with about 5 mg/m$^2$ to about 200 mg/m$^2$ cisplatin. For example, one embodiment includes administration of cisplatin at a dose of about 50 or 70 mg/m$^2$ once every 3 to 4 weeks. One embodiment includes administration of cisplatin at a dose of about 50 or 70 mg/m$^2$ once every 3 weeks. Another embodiment includes administration of cisplatin at a dose of about 75 or 100 mg/m$^2$ once every 3 weeks. In another embodiment, administration of cisplatin is at a dose of about 20 mg/m$^2$ daily for upto 5 days. The administration of cisplatin can be made by intravenous infusion, intravenous push, bolus injection or subcutaneous injection. In one embodiment, the administration of cisplatin is once every 3 to 4 weeks, while the administration of SNS-595 occurs once per week for three weeks or once every three weeks. In one embodiment, the administration of cisplatin is daily for 5 days, while the administration of SNS-595 occurs once per week for three weeks or once every three weeks. In one embodiment, the administration of cisplatin is once a week for 3 weeks, while the administration of SNS-595 occurs once per week for three weeks or once every three weeks.

In one embodiment, the methods provided include the administration of SNS-595, or a pharmaceutically acceptable salt, solvate or hydrate thereof thereof in combination with about 50 mg/m$^2$ to about 400 mg/m$^2$ carboplatin. For example, one embodiment includes administration of carboplatin at a dose of about 300 or about 360 mg/m$^2$ once every 3 weeks. One embodiment includes administration of carboplatin at a dose of about 300 or 360 mg/m² once every 4 weeks. The administration of carboplatin can be made by intravenous infusion, intravenous push, bolus injection or subcutaneous injection. In one embodiment, the administration of carboplatin is once every 3 weeks, while the administration of SNS-595 occurs once per week for three weeks or once every three weeks. In one embodiment, the administration of carboplatin is once a week for 3 weeks, while the administration of SNS-595 occurs once per week for three weeks or once every three weeks.

In one embodiment, the methods provided include the administration of SNS-595, or a pharmaceutically acceptable salt, solvate or hydrate thereof thereof in combination with about 100 mg/m² to about 1500 mg/m² gemcitabine. For example, one embodiment includes administration of gemcitabine at a dose of about 1000 or 1250 mg/m² once every week for at least 4 weeks. The administration of gemcitabine can be made by intravenous infusion, intravenous push, bolus injection or subcutaneous injection. In one embodiment, the administration of gemcitabine is once a week for up to 4 weeks, while the administration of SNS-595 occurs once per week for three weeks or once every three weeks. In one embodiment, the administration of gemcitabine is twice a week for 2 weeks, while the administration of SNS-595 occurs once per week for three weeks.

As discussed herein, the administration of SNS-595 and the second agents as set forth above in a week is considered a weekly cycle. The methods contemplate performing one weekly cycle, optionally waiting a period of one week to several weeks where neither the second agent nor SNS-595 is given, then repeating a weekly cycle. The methods also contemplate repeating the weekly cycles continuously, for example, for 3 to 5 weeks. In addition, the methods contemplate repeating the cycle for several cycles, waiting a period of a week to several weeks where neither SNS-595 nor the second agent is given then repeating one or more cycles. Finally, the methods provide administration of a SNS-595/second agent weekly cycle followed by a cycle of only the second agent or SNS-595.

4. BRIEF DESCRIPTION OF DRAWINGS

Figure 2:
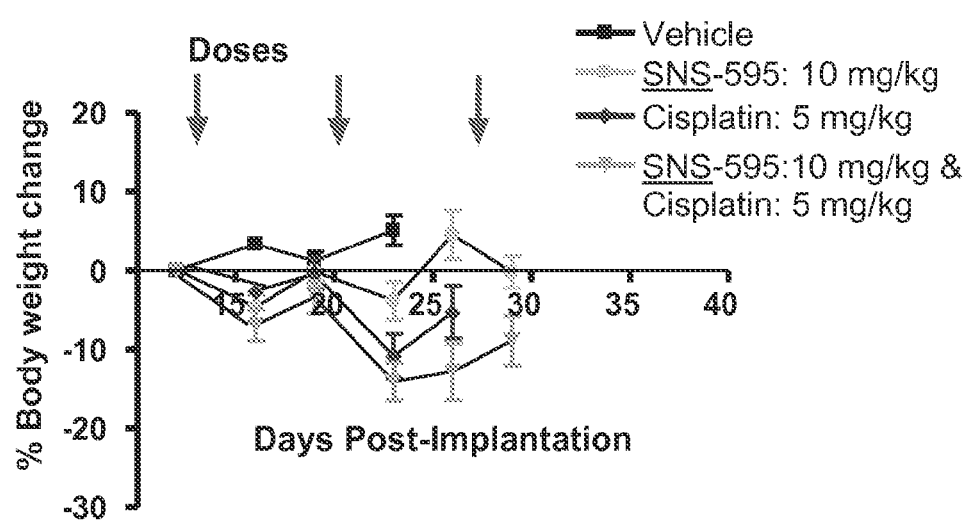
Figure 3:
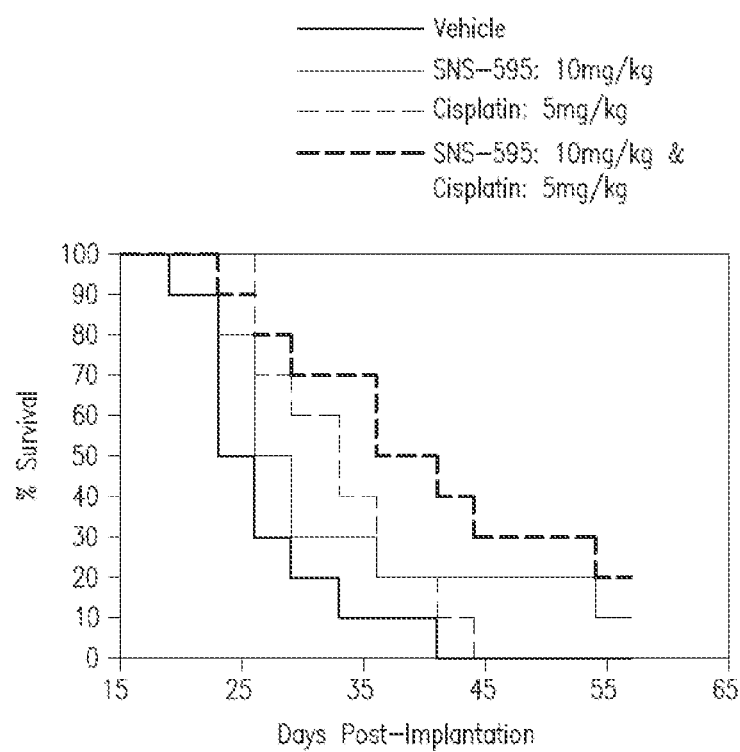
Figure 4:
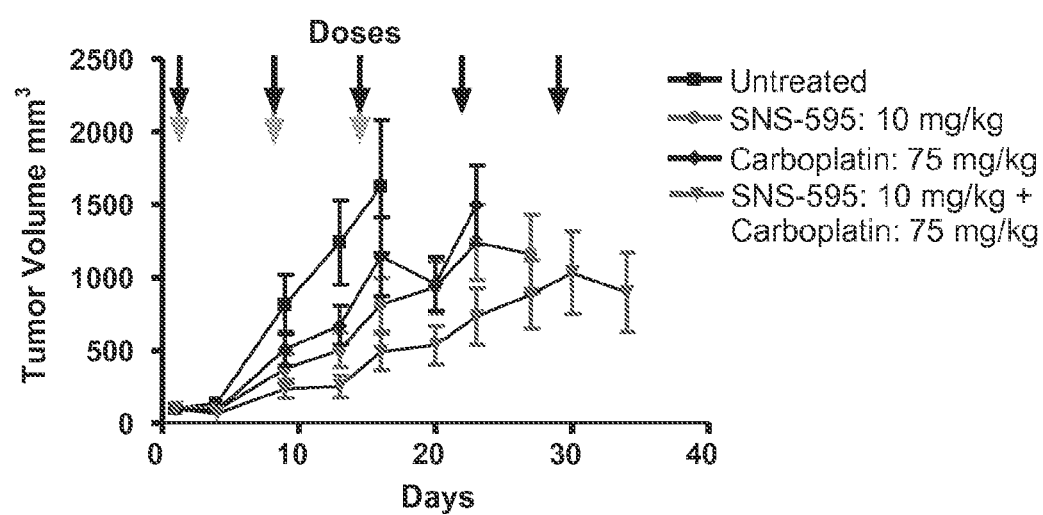
Figure 5:
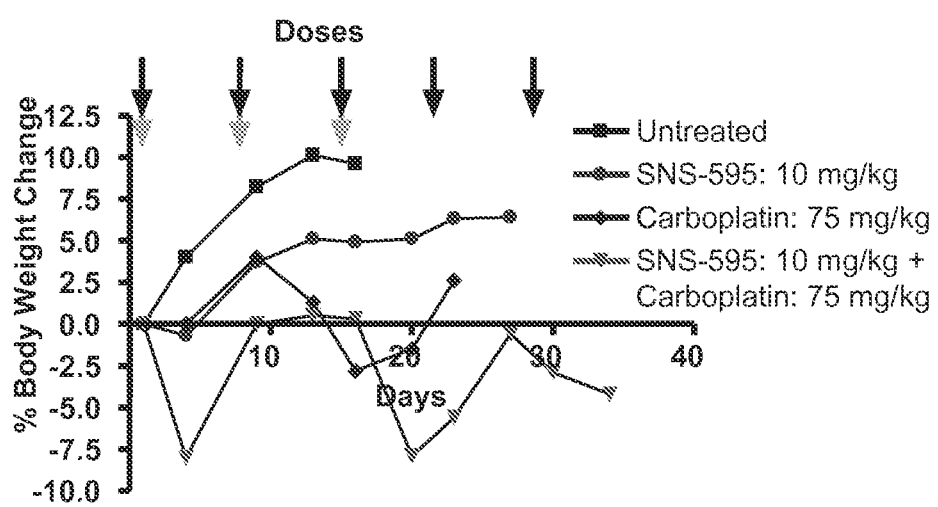
Figure 6:
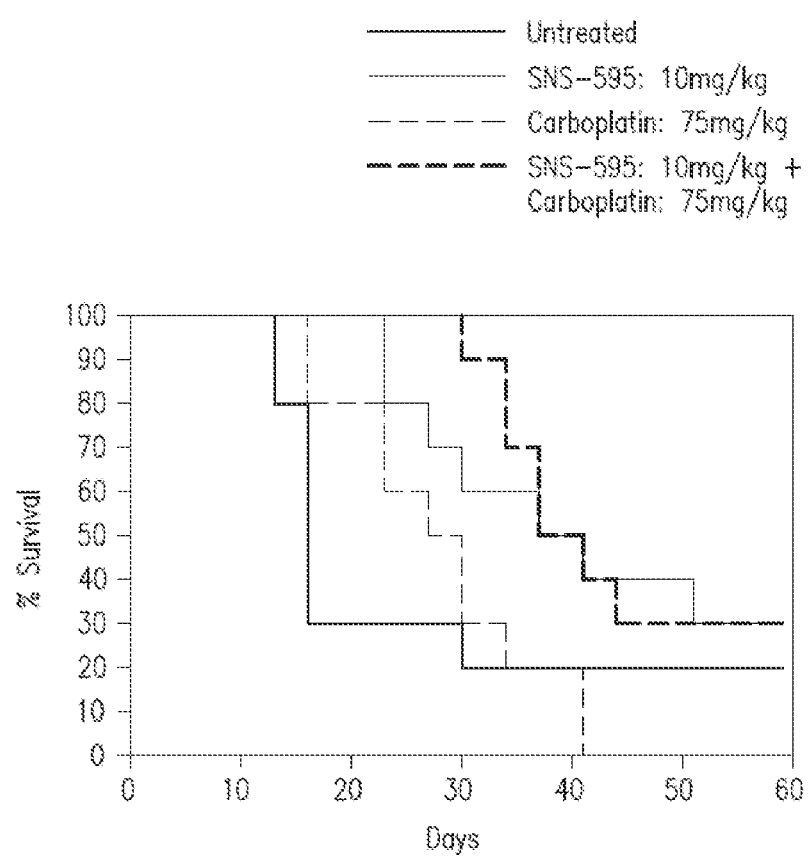
Figure 7:
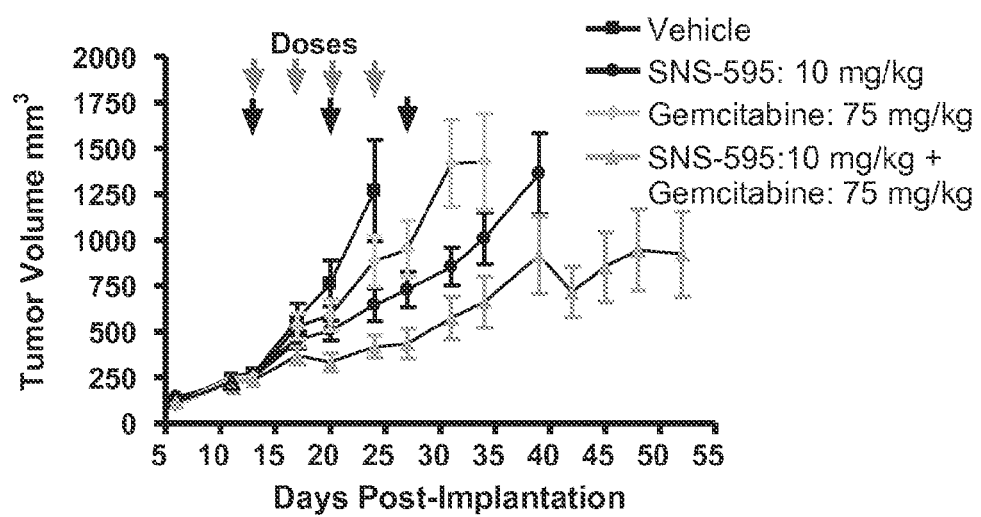
Figure 8:
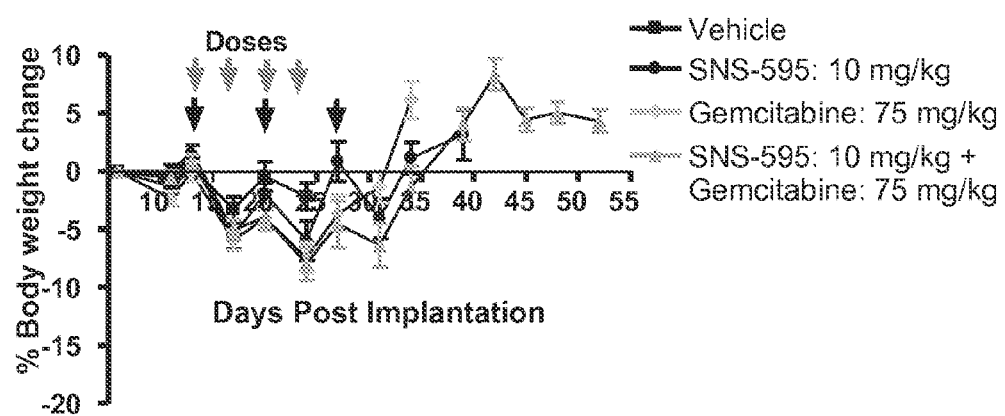
Figure 9:
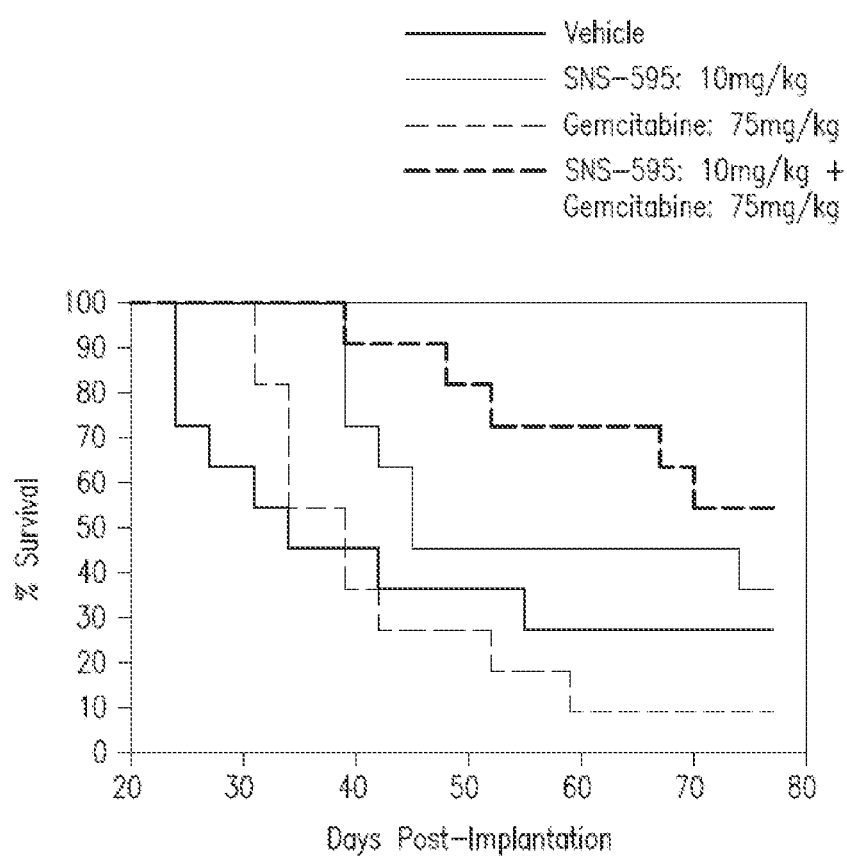
Figure 10:
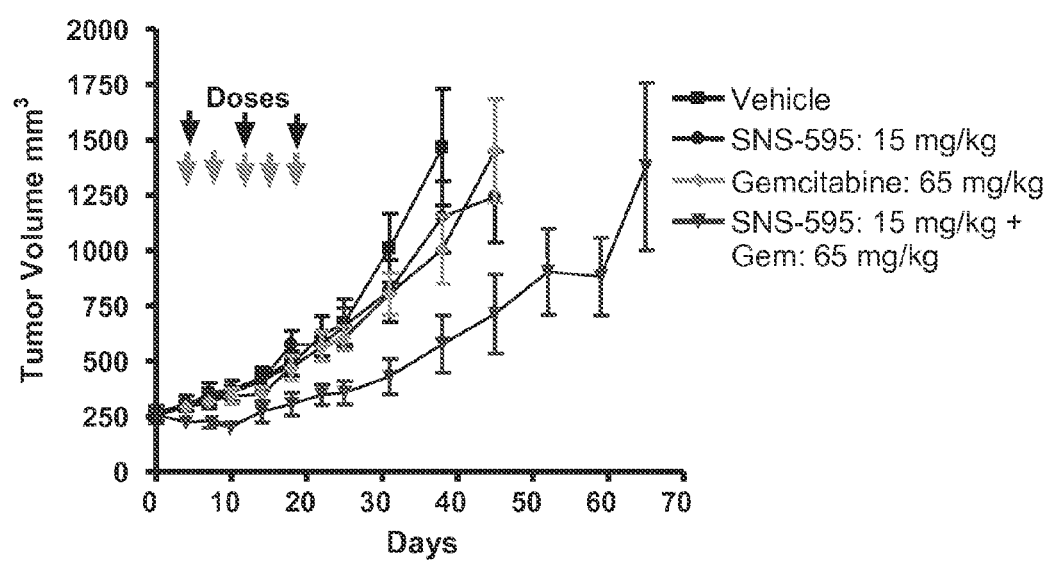
Figure 11:
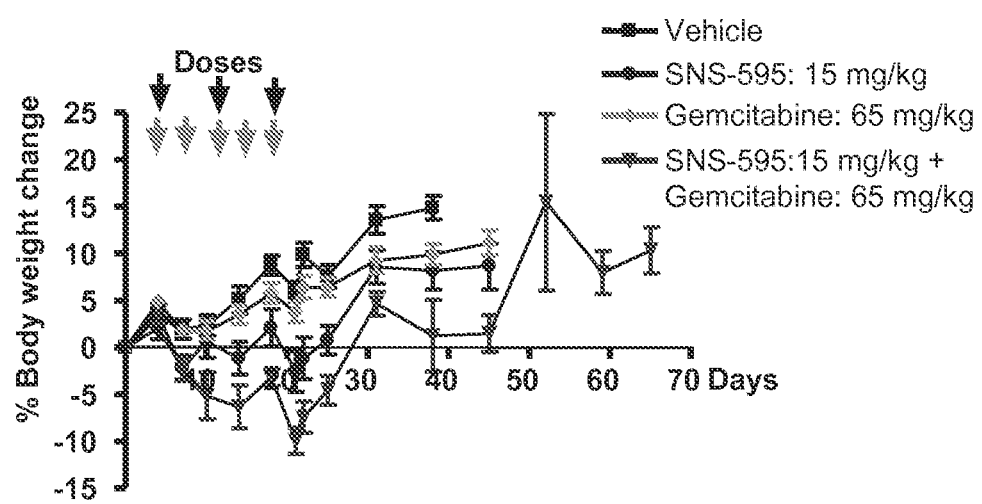
Figure 12:
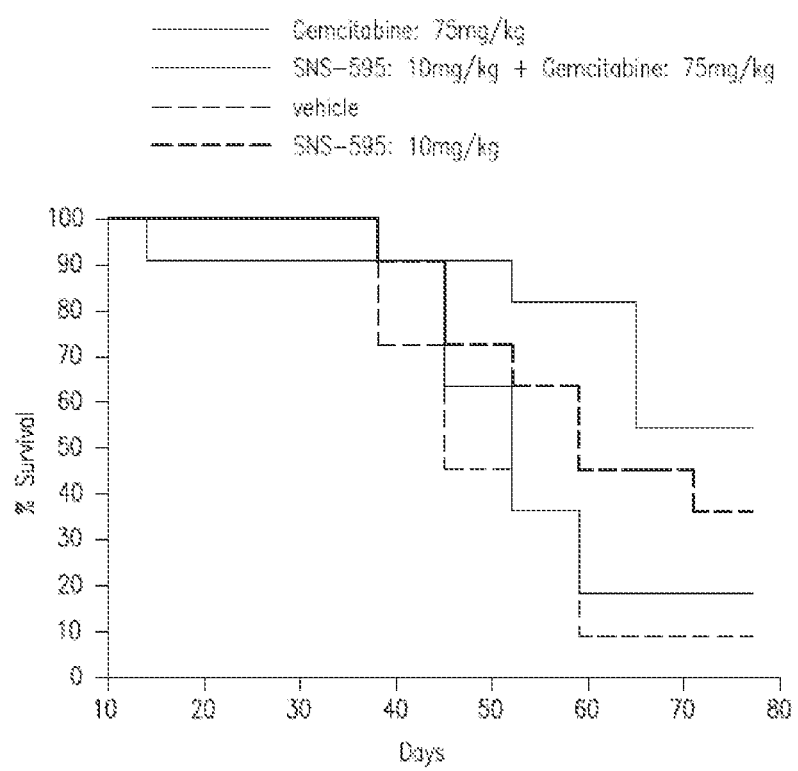

FIG. 1: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and cisplatin on tumor volume in an ovarian cancer xenograft model (treatment with SNS-595 is indicated with black arrows and cisplatin with gray arrows);

FIG. 2: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and cisplatin on % body weight change in an ovarian cancer xenograft model; (treatment with SNS-595 is indicated with black arrows and cisplatin with gray arrows);

FIG. 3 provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and cisplatin on % survival in an ovarian cancer xenograft model;

FIG. 4: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and carboplatin on tumor volume in a non small cell lung cancer xenograft model (treatment with SNS-595 is indicated with black arrows and carboplatin with gray arrows);

FIG. 5: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and carboplatin on % body weight change in a non small cell lung cancer xenograft model (treatment with SNS-595 is indicated with black arrows and carboplatin with gray arrows);

FIG. 6: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and carboplatin on % survival in a non small cell lung cancer xenograft model;

FIG. 7: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and gemcitabine on tumor volume in a non small cell lung cancer xenograft model (treatment with SNS-595 is indicated with black arrows and gemcitabine with gray arrows);

FIG. 8: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and gemcitabine on % survival in a non small cell lung cancer xenograft model (treatment with SNS-595 is indicated with black arrows and gemcitabine with gray arrows);

FIG. 9: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and gemcitabine on % body weight change in a non small cell lung cancer xenograft model;

FIG. 10: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and gemcitabine on the tumor volume in a pancreatic cancer xenograft model (treatment with SNS-595 is indicated with black arrows and gemcitabine with gray arrows);

FIG. 11: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and gemcitabine on % survival in a pancreatic cancer xenograft model (treatment with SNS-595 is indicated with black arrows and gemcitabine with gray arrows); and FIG. 12: provides the effect of treatment with (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) and gemcitabine on % body weight change in a pancreatic cancer xenograft model.

In the figures, 595 refers to (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595).

5. DETAILED DESCRIPTION OF THE INVENTION

Provided herein are methods of treating, managing, or preventing cancers comprising administering to a subject, such as a mammal in need of such treatment, management or prevention a therapeutically or prophylactically effective amount of SNS-595, or a pharmaceutically acceptable salt, solvate or hydrate thereof thereof in combination with a second agent selected from carboplatin, cisplatin, and gemcitabine. In one embodiment, the methods encompass treating, preventing or managing various cancers selected from bladder cancer, breast cancer, cervical cancer, colon cancer (including colorectal cancer), esophageal cancer, head and neck cancer, liver cancer, lung cancer (both small cell and non-small cell), melanoma, myeloma, neuroblastoma (i.e., CNS cancer), ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer. The cancer can be relapsed, refractory or resistant to conventional therapy.

In the methods provided herein, SNS-595, or a pharmaceutically acceptable salt, solvate or hydrate thereof thereof is administered in combination with a second active agent selected from carboplatin, cisplatin and gemcitabine. Specific doses and dosing regimens for these combinations are provided below.

5.1 Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is substantially free from (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (i.e., in enantiomeric excess). In other words, the "(+)" form of 1,4-dihydro-7-[(3S,4S)-3-methoxy-4-(methylamino)-1-pyrrolidinyl]-4-oxo-1-(2-thiazolyl)-1,8-naphthyridine-3-carboxylic acid is substantially free from the "(−)" form of the compound and is, thus, in enantiomeric excess of the "(−)" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, or more than 97% by weight of the enantiomer.

As used herein and unless otherwise indicated, the term "enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid" refers to at least about 80% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 20% by weight (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, at least about 90% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 10% by weight the (−)-enantiomer, at least about 95% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 5% by weight the (−)-enantiomer, at least about 97% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 3% by weight (−)-enantiomer.

As used herein and unless otherwise indicated, the terms "treat," "treating" and "treatment" refer to alleviating or reducing the severity of a symptom associated with the disease or condition being treated.

The term "prevention" includes the inhibition of a symptom of the particular disease or disorder. In some embodiments, patients with familial history of cancer or leukemia are candidates for preventive regimens. Generally, the term "preventing" refers to administration of the drug prior to the onset of symptoms, particularly to patients at risk of cancer.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" is an animal, typically a mammal, including a human, such as a human patient.

As used herein, the term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endrometrium, esophagus, eye, head, kidney, liver, lung, mouth, neck, ovaries, pancreas, prostate, rectum, stomach, testis, throat, and uterus.

The term "relapsed" refers to a situation where patients who have had a remission of cancer after therapy have a return of cancer cells.

The term "refractory or resistant" refers to a circumstance where patients, even after intensive treatment, have residual cancer cells in their body.

As used herein and unless otherwise indicated, the term "pharmaceutically acceptable salt" includes, but is not limited to, salts of acidic or basic groups that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate thereof and the like).

As used herein, and unless otherwise specified, the terms "second agent" or "second active agent" refer to cisplatin, carboplatin or gemcitabine or a combination thereof.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of two therapeutic agents (for example, SNS-595 and a second anti-cancer agent, such as carboplatin, cisplatin, and gemcitabine) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "supportive care agent" refers to any substance that treats, prevents or manages an adverse effect from SNS-595 treatment.

The term "about," as used herein, unless otherwise indicated, refers to a value that is no more than 10% above or below the value being modified by the term. For example, the term "about 10 mg/m$^2$" means a range of from 9 mg/m$^2$ to 11 mg/m$^2$.

5.2 SNS-595

The compound for use in the methods and compositions provided herein is enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, which is also known as SNS-595 or AG-7352. SNS-595 has the following chemical structure:

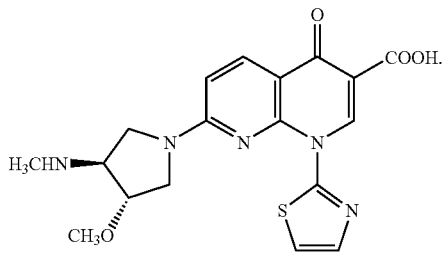

In certain embodiments, pharmaceutically acceptable salts, solvates, hydrates or prodrugs of SNS-595 are used in the methods and compositions provided herein.

SNS-595 can be prepared by methods known to one of skill in the art, for example, according to the preparation procedure for Example C-1 of U.S. Pat. No. 5,817,669, entitled "Compounds, processes for the preparation thereof and anti-tumor agents," issued Oct. 6, 1998, and in Japanese Patent Application No. Hei 10-173986, to Chikugi et al., which are incorporated herein by reference in their entireties. Certain exemplary pharmaceutical compositions comprising SNS-595 and methods of using the same are described in U.S. Patent Application Pub. Nos. 2005/0203120; 2005/0215583, 2006/0025437, 2006/0063795 and 2006/0247267, and 2008-0063642 and International Publication No. WO 2007/028171, which are incorporated herein by reference in their entireties.

5.3 Second Active Agents

In the methods and compositions provided herein, SNS-595 or a pharmaceutically acceptable salt, solvate or hydrate thereof thereof can be used with or combined with second active agents. Without being limited by any theory, it is believed that certain combinations work synergistically in the treatment of cancers. The methods also encompass the use of SNS-595 or a pharmaceutically acceptable salt, solvate or hydrate thereof thereof in a manner to alleviate, reduce or avoid adverse effects associated with certain second active agents. Also provided are methods, wherein the second active agents are used in the manner to alleviate, reduce or avoid adverse or unwanted effects associated with SNS-595 or a pharmaceutically acceptable salt, solvate or hydrate thereof thereof including dose limiting toxicity.

One or more second active ingredients or agents can be used together with SNS-595 in the methods and compositions provided herein. In certain embodiments, the second active agent is selected from carboplatin, cisplatin, and gemcitabine.

In the combination therapy provided herein, SNS-595 and the second agent can be administered simultaneously or sequentially with SNS-595. In certain embodiments, SNS-595 and the second agent selected from carboplatin, cisplatin, and gemcitabine are used in combination methods that may also include the use of one or more other therapies including, but not limited to, treatment with a therapeutic antibody that specifically binds to a cancer antigen, hematopoietic growth factor, cytokine, other anti-cancer agent, antibiotic, cox-2 inhibitor, immunomodulatory agent, immunosuppressive agent, corticosteroid or a pharmacologically active mutant or derivative thereof, anti-cancer agents, radiation therapy, antiemetics and the like.

In certain embodiments, use of a second active agent in combination with SNS-595 may be modified or delayed during or shortly following administration of SNS-595 as deemed appropriate by the practitioner of skill in the art. In certain embodiments, subjects being administered SNS-595 in combination with the second agents may receive supportive care including antiemetics, when appropriate. In some embodiments, subjects being administered SNS-595 in combination with the second agents may be administered a growth factor as a third active agent according to the judgment of the practitioner of skill in the art. In some embodiments, provided is administration of SNS-595 and the second agent in combination with erythropoietin or darbepoetin (Aranesp). In certain embodiments, administration of erythropoietin or darbepoetin is delayed during administration of SNS-595, the second agent or both. In certain embodiments, erythropoietin or darbepoetin is administered during administration of SNS-595, for instance when the subject presents anemia or severe anemia. In some embodiments, administration of prophylactic granulocyte-macrophage colony-stimulating factor (GM-CSF); sargramostim (Leukine®), molgramostim, (Leukomax) or granulocyte colony-stimulating factor (G-CSF); filgrastim (Neupogen®), pegfilgrastim (Neulasta®) is delated during one or more administrations of SNS-595. In certain embodiments, provided are method for administrations of prophylactic granulocyte-macrophage colony-stimulating factor (GM-CSF); sargramostim (Leukine®), molgramostim, (Leukomax) or granulocyte colony-stimulating factor (G-CSF); filgrastim (Neupogen®), pegfilgrastim (Neulasta®) permitted after administration of SNS-595, for instance in a subject experiencing neutropenia or recurrent neutropenia. In certain embodiments, provided is administration of myeloid growth factors in combination with SNS-595, for instance in a subject with a serious neutropenic complication, such as tissue infection, sepsis syndrome, or fungal infection, or at the discretion of the practitioner of skill.

In certain embodiments, the methods provided herein further comprise administration of one or more of the following: oral allopurinol, Rasburicase, Leukapheresis (for istance, administered up to 72 hours after the first treatment with SNS-595 Injection), and any other medication deemed appropriate by the practitioner of skill in the art.

5.4 Methods of Treatment and Prevention

The methods provided herein encompass treating, preventing or managing various solid tumors, including, but not limited to, the bladder cancer, breast cancer, cervical cancer, colon cancer (including colorectal cancer), esophageal cancer, head and neck cancer, liver cancer, lung cancer (both small cell and non-small cell), melanoma, myeloma, neuroblastoma (i.e., CNS cancer), ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer. The methods comprise the step of administering to the subject a therapeutically effective amount of an enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (SNS-595) or a pharmaceutically acceptable salt, solvate or hydrate thereof thereof in combination with a therapeutically effective amount of a second active agent selected from carboplatin, cisplatin and gemcitabine. In one embodiment, the second active agent is gemcitabine. In one embodiment, the second active agent is carboplatin. In one embodiment, the second active agent is cisplatin.

5.4.1 Combination Therapy with a Second Active Agent

In certain embodiments, the methods provided herein comprise administering SNS-595 in combination with one or more second active agents, and further in combination with radiation therapy, therapy with other anti-cancer agents or surgery. The administration of SNS-595 and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., *Physicians' Desk Reference*, 1755-1760 (56$^{th}$ ed., 2002).

The second active agent may be administered simultaneously, at essentially the same time, or sequentially with SNS-595. If administration takes place sequentially, second active agent may be administered before or after administration of SNS-595. In some embodiments, the second active agent is administered before administration of SNS-595. In some embodiments, the second active agent is administered simultaneously with administration of SNS-595. In some embodiments, the second active agent is administered after the administration of SNS-595. SNS-595 and the second active agent need not be administered by means of the same vehicle. In some embodiments, the second active agent and SNS-595 are administered in different vehicles. In embodiments of the methods described herein where delivery of SNS-595 and the second active agent are both by an intravenous route of administration, administration of each component of the combination need not be administered in the same IV line. In some embodiments, SNS-595 is administered in a different IV line than the second active agent. The second active agent may be administered one or more times, and the number of administrations of each component of the combination may be the same or different. In addition, SNS-595 and the second active agent need not be administered at the same site.

In one embodiment, SNS-595 can be administered in an amount of from about 1 to about 150 mg/m$^2$, about 1 to about 120 mg/m$^2$, about 1 to about 100 mg/m$^2$, about 1 to about 75 mg/m$^2$, about 1 to about 60 mg/m$^2$, about 1 to about 50 mg/m$^2$, about 3 to about 30 mg/m$^2$, about 3 to about 24 mg/m$^2$ in combination with a second active agent disclosed herein. In another specific embodiment, SNS-595 is administered at a dose of about 10 to about 90 mg/m$^2$.

In another embodiment, the methods provided herein comprise administering to a patient in need thereof, a dose of about 1 mg/m$^2$-150 mg/m$^2$ of SNS-595 and a therapeutically effective amount of a second agent selected from cisplatin, carboplatin and gemcitabine and further administering a therapeutically effective amount of a supportive care agent. Such supportive care agents are known in the art, for example, see, U.S. Application Publication No. 2006/0025437, which is incorporated by reference in its entirety.

In certain embodiments, the combination dosing of SNS-595 and the second agent is used together as well with supportive care agents or other auxillary therapies. While not intending to be bound by any particular theory of operation, it is believed that SNS-595 and the second agent can act synergistically in the methods provided herein. Exemplary dosing schedules for the combination dosing of SNS-595 and the second agent are provided below.

5.5 Pharmaceutical Compositions and Dosage Forms

The methods provided herein use pharmaceutical compositions containing SNS-595 and/or a pharmaceutically acceptable salt, solvate or hydrate thereof thereof and pharmaceutically acceptable carriers, such as diluents or adjuvants, or in combination with a second agent. In clinical practice SNS-595 and/or a pharmaceutically acceptable salt, solvate or hydrate thereof may be administered by any conventional route, including but not limited to orally, parenterally, rectally or by inhalation (e.g. in the form of aerosols). In one embodiment, SNS-595 and/or a pharmaceutically acceptable salt, solvate or hydrate thereof is administered by an IV injection.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

Pharmaceutical compositions can be used in the preparation of individual, single unit dosage forms. Pharmaceutical compositions and dosage forms comprise SNS-595 and one or more excipients.

Pharmaceutical compositions and dosage forms can also comprise one or more additional active ingredients. Examples of second, or additional, active ingredients are disclosed herein.

In certain embodiments, a composition provided herein is a pharmaceutical composition or a single unit dosage form. Pharmaceutical compositions and single unit dosage forms provided herein comprise a prophylactically or therapeutically effective amount of SNS-595, and typically one or more pharmaceutically acceptable carriers or excipients. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In certain embodiments, water is a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in *Remington: The Science and Practice of Pharmacy*, 21$^{St}$ edition, Lippincott, Williams and Wilkins, Baltimore, Md. (2005), the contents of which are hereby incorporated by reference in their entirety.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Further provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, powders and the like. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a subject, such an animal subject, including a mammalian subject, or in particular a human subject.

A pharmaceutical composition provided herein is formulated to be compatible with its intended route of administration. Examples of routes of administration include, but are not limited to, parenteral, e.g., intravenous, intradermal, intramuscular, subcutaneous, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, intranasal or topical administration to human beings. In one embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Examples of dosage forms include, but are not limited to: liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of disease may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., *Remington: The Science and Practice of Pharmacy*, 21$^{St}$ edition, Lippincott, Williams and Wilkins, Baltimore, Md. (2005), the contents of which are hereby incorporated by reference in their entirety.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms provided herein comprise SNS-595 within the range of about 1 mg to about 150 mg per vial. Particular dosage forms provided herein have about 1, 3, 6, 9, 10, 12, 13.5, 15, 18, 19, 21, 24, 25, 27, 30, 38, 45, 50, 60, 63, 70, 75, 80, 85, 90, 95, 100, 105; 110, 115, 120, 125, 130, 135, 140, 145 or 150 mg of SNS-595 per vial.

5.5.1 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of active ingredients. See, e.g., U.S. Pat. No. 5,134,127, which is incorporated herein by reference.

5.6 Exemplary Dosages

In one embodiment, the methods of treating, preventing or managing cancers provided herein comprise administering to a patient SNS-595 and/or a pharmaceutically acceptable salt, solvate or hydrate thereof in combination with a second active agent, on the basis of body surface area. Body surface area calculations can be calculated for example, with the Mosteller formula wherein:

$$BSA(m^2) = \text{square root of } [(\text{height(cm)} \times \text{weight(kg)})/3600].$$

In one embodiment, SNS-595 and/or a pharmaceutically acceptable salt, solvate or hydrate thereof can be administered orally or intravenously and in single or divided daily doses in an amount of about 1 to about 150 mg/m$^2$. Certain exemplary doses per day include about 1, 3, 6, 9, 10, 12, 13.5, 15, 18, 19, 21, 24, 25, 27, 30, 38, 45, 50, 60, 63, 75, 80, 85, 90, 95, 100, 105, 110, 115, 120, 125, 130, 135, 140, 145 or 150 mg/m$^2$.

In another embodiment, the methods comprise administering a dose of about 3 mg/m$^2$-120 mg/m$^2$ of SNS-595 and/or a pharmaceutically acceptable salt, solvate or hydrate thereof. In another embodiment, the dose is about 10 mg/m$^2$-100 mg/m$^2$. In another embodiment, the dose is about 30 mg/m$^2$-75 mg/m$^2$. In another embodiment, the dose is about 40 mg/m$^2$-80 mg/m$^2$. In another embodiment, the dose is about 50 mg/m$^2$-90 mg/m$^2$. In another embodiment, the dose is about 15 mg/m$^2$-80 mg/m$^2$.

In another embodiment the dose of SNS-595 and/or a pharmaceutically acceptable salt, solvate or hydrate thereof is about 20 mg/m$^2$-30 mg/m$^2$. In another embodiment the dose is about 25 mg/m$^2$-35 mg/m$^2$. In another embodiment the dose is about 40 mg/m$^2$-50 mg/m$^2$. In another embodiment the dose is about 45 mg/m$^2$-55 mg/m$^2$. In another embodiment the dose is about 50 mg/m$^2$-60 mg/m$^2$. In another embodiment the dose is about 55 mg/m$^2$-65 mg/m$^2$. In another embodiment the dose is about 60 mg/m$^2$-70 mg/m$^2$. In another embodiment the dose is about 65 mg/m$^2$-75 mg/m$^2$. In another embodiment the dose is about 70 mg/m$^2$-80 mg/m$^2$. In another embodiment the dose is about 75 mg/m$^2$-85 mg/m$^2$. In another embodiment the dose is about 80 mg/m$^2$-90 mg/m$^2$. In another embodiment the dose is about 85 mg/m$^2$-95 mg/m$^2$. In another embodiment the dose is about 90 mg/m$^2$-100 mg/m$^2$. In another embodiment the dose is about 100 mg/m$^2$-110 mg/m$^2$. In another embodiment the dose is about 110 mg/m$^2$-120 mg/m$^2$. In another embodiment the dose is about 120 mg/m$^2$-130 mg/m$^2$.

In another embodiment, the dose of SNS-595 and/or a pharmaceutically acceptable salt, solvate or hydrate thereof is about 1 mg/m$^2$-75 mg/m$^2$. In another embodiment, the dose is about 1 mg/m$^2$-60 mg/m$^2$. In another embodiment, the dose is about 1 mg/m$^2$-48 mg/m$^2$. In another embodiment, the dose is about 3 mg/m$^2$-24 mg/m$^2$. In another embodiment, the dose is about 3 mg/m$^2$-18 mg/m$^2$. In another embodiment, the dose is about 3 mg/m$^2$-15 mg/m$^2$.

In another embodiment, the dose of SNS-595 and/or a pharmaceutically acceptable salt, solvate or hydrate thereof is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, 33 mg/m$^2$, 34 mg/m$^2$, 35 mg/m$^2$, 36 mg/m$^2$, 37 mg/m$^2$, 38 mg/m$^2$, 39 mg/m$^2$, 40 mg/m$^2$, 41 mg/m$^2$, 42 mg/m$^2$, 43 mg/m$^2$, 44 mg/m$^2$, 45 mg/m$^2$, 46 mg/m$^2$, 47 mg/m$^2$, 48 mg/m$^2$, 49 mg/m$^2$, 50 mg/m$^2$, 55 mg/m$^2$, 60 mg/m$^2$, 65 mg/m$^2$, 75 mg/m$^2$ or 90 mg/m$^2$.

The administered dose of SNS-595 and/or a pharmaceutically acceptable salt, solvate or hydrate thereof can be delivered as a single dose (e.g. a single bolus IV injection) or over a 24-hour period (e.g., continuous infusion over time or divided bolus doses over time) and is repeated until the patient experiences stable disease or regression, or until the patient experiences disease progression or unacceptable toxicity. Stable disease or lack thereof is determined by methods known in the art, such as evaluation of patient symptoms, physical examination and other commonly accepted evaluation modalities.

The administered dose of SNS-59 and/or a pharmaceutically acceptable salt, solvate or hydrate thereof 5 can be expressed in units other than as mg/m$^2$. For example, doses can be expressed as mg/kg. One of ordinary skill in the art would readily know how to convert doses from mg/m$^2$ to mg/kg to given either the height or weight of a subject or both (see, e.g., www.fda.gov/cder/cancer/animalframe.htm). For example, a dose of 10 mg/m$^2$-150 mg/m$^2$ for a 65 kg human is approximately equal to 0.26 mg/kg-3.95 mg/kg. In another example, a dose of 15 mg/m$^2$-80 mg/m$^2$ for a 65 kg human is approximately equal to 0.39 mg/kg-2.11 mg/kg.

In certain embodiments, SNS-595 and/or a pharmaceutically acceptable salt, solvate or hydrate thereof is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

In one embodiment, the methods provided herein comprise: i) administering a dose of about 10 mg/m$^2$-120 mg/m$^2$ of SNS-595 and/or a pharmaceutically acceptable salt, solvate or hydrate thereof to a mammal; ii) waiting a period of at least one day where the mammal is not administered any SNS-595 and/or a pharmaceutically acceptable salt, solvate or hydrate thereof; iii) administering another dose of about 10 mg/m$^2$-120 mg/m$^2$ of SNS-595 and/or a pharmaceutically acceptable salt, solvate or hydrate thereof to the mammal; and, iv) repeating steps ii)-iii) a plurality of times.

In one embodiment, the methods provided herein comprise: i) administering a dose of about 10 mg/m$^2$-90 mg/m$^2$ of SNS-595 and/or a pharmaceutically acceptable salt, solvate or hydrate thereof to a mammal; ii) waiting a period of at least one day where the mammal is not administered any SNS-595 and/or a pharmaceutically acceptable salt, solvate or hydrate thereof iii) administering another dose of about 10 mg/m$^2$-90 mg/m$^2$ of SNS-595 and/or a pharmaceutically acceptable salt, solvate or hydrate thereof to the mammal; and, iv) repeating steps ii)-iii) a plurality of times.

In one embodiment, the methods provided herein comprise: i) administering a dose of about 10 mg/m²-70 mg/m² of SNS-595 and/or a pharmaceutically acceptable salt, solvate or hydrate thereof to a mammal; ii) waiting a period of at least one day where the mammal is not administered any SNS-595 and/or a pharmaceutically acceptable salt, solvate or hydrate thereof; iii) administering another dose of about 10 mg/m²-70 mg/m² of SNS-595 and/or a pharmaceutically acceptable salt, solvate or hydrate thereof to the mammal; and, iv) repeating steps ii)-iii) a plurality of times In one embodiment, the dose SNS-595 and/or a pharmaceutically acceptable salt, solvate or hydrate thereof is about 15 mg/m² once a week for three weeks. In one embodiment, the dose SNS-595 and/or a pharmaceutically acceptable salt, solvate or hydrate thereof is about 18 mg/m² once a week for three weeks. In one embodiment, the dose SNS-595 and/or a pharmaceutically acceptable salt, solvate or hydrate thereof is about 48 mg/m² once every three weeks. In one embodiment, the dose SNS-595 and/or a pharmaceutically acceptable salt, solvate or hydrate thereof is about 60 mg/m² once every three weeks. In one embodiment, the dose SNS-595 and/or a pharmaceutically acceptable salt, solvate or hydrate thereof is about 90 mg/m² once every three weeks.

5.6.1 Exemplary Dosages: Combination Dosing of SNS-595 and Second Agents

The methods provided herein comprise administering SNS-595 and/or a pharmaceutically acceptable salt, solvate or hydrate thereof in combination with one or more second active agents selected from carboplatin, cisplatin and gemcitabine. The second agents provided herein can be administered either prior to, concurrently with, or subsequent to administration of SNS-595 and/or a pharmaceutically acceptable salt, solvate or hydrate thereof. In some embodiments, the second agent can be administered subcutaneously or intravenously. In certain embodiments, the second agent is administered subcutaneously. In certain embodiments, the second agent is administered intravenously.

Combination of SNS-595 and Cisplatin

In one embodiment, the second agent is cisplatin and the dose of cisplatin is about 5 mg/m² to about 200 mg/m², about 5 mg/m² to about 150 mg/m², about 10 mg/m² to 100 mg/m², about 20 mg/m² to 80 mg/m², about 50 mg/m² to 70 mg/m² or about 75 mg/m² to 100 mg/m². In another embodiment, the dose of cisplatin is about 20 mg/m². In another embodiment, the dose of cisplatin is about 75 mg/m² to 100 mg/m². In certain embodiments, cisplatin can be administered continuously, by bolus injection, or by divided bolus injections over a particular time period such as, for example, one day.

In some embodiments, the methods of treating cancer comprise administering from about 1 mg/m² to about 150 mg/m² of SNS-595 and about 20 mg/m² to about 100 mg/m² of cisplatin. In certain embodiments, the methods comprise administering about 10 mg/m² SNS-595 and about 20 mg/m² of cisplatin; about 15 mg/m² SNS-595 and about 18 mg/m² of cisplatin; about 30 mg/m² SNS-595 and about 20 mg/m² of cisplatin; about 48 mg/m² SNS-595 and about 20 mg/m² of cisplatin; about 60 mg/m² SNS-595 and about 20 mg/m² of cisplatin; about 75 mg/m² SNS-595 and about 20 mg/m² of cisplatin; or about 90 mg/m² SNS-595 and about 20 mg/m² of cisplatin.

In certain embodiments, the methods comprise administering about 10 mg/m² SNS-595 and from about 50 to 70 mg/m² of cisplatin; about 15 mg/m² SNS-595 and from about 50 to 70 mg/m² of cisplatin; about 30 mg/m² SNS-595 and from about 50 to 70 mg/m² of cisplatin; about 48 mg/m² SNS-595 and from about 50 to 70 mg/m² of cisplatin; about 60 mg/m² SNS-595 and from about 50 to 70 mg/m² of cisplatin; about 75 mg/m² SNS-595 and from about 50 to 70 mg/m² of cisplatin; or about 90 mg/m² SNS-595 and from about 50 to 70 mg/m² of cisplatin.

In certain embodiments, the methods comprise administering about 10 mg/m² SNS-595 and from about 75 to 100 mg/m² of cisplatin; about 15 mg/m² SNS-595 and from about 75 to 100 mg/m² of cisplatin; about 18 mg/m² SNS-595 and from about 75 to 100 mg/m² of cisplatin; about 48 mg/m² SNS-595 and from about 75 to 100 mg/m² of cisplatin; about 60 mg/m² SNS-595 and from about 75 to 100 mg/m² of cisplatin; about 75 mg/m² SNS-595 and from about 75 to 100 mg/m² of cisplatin; or about 90 mg/m² SNS-595 and from about 75 to 100 mg/m² of cisplatin.

In certain embodiments, the methods of treating, preventing or managing a cancer comprises administering a total dosage of about 10 mg/m²-120 mg/m² SNS-595, in one embodiment, about 10-80 mg/m² SNS-595 in combination with a continuous intravenous dose of about 5 mg/m²/day-30 mg/m²/day if cisplatin for 5 days, in one embodiment, about 20 mg/m²/day of cisplatin for a 5 day period, wherein the 5-day period comprises a treatment cycle. In some embodiments, the method comprises administering a total dosage of about 20 mg/m²-60 mg/m² SNS-595 in combination with a continuous intravenous dose of about 20 mg/m²/day cisplatin over a 5-day period, wherein the 5-day period comprises a treatment cycle. In some embodiments, the treatment cycle is repeated at least once. In some embodiments, the treatment cycle is repeated at least twice. In some embodiments, the treatment cycle is repeated at least three times. In some embodiments, the treatment cycle is repeated at least four times.

In certain embodiments, the methods of treating, preventing, or managing a cancer comprises administering a total weekly amount of about 10-120 mg/m² SNS-595 in combination with a total daily amount of about 10-50 mg/m² cisplatin.

In certain embodiments, cisplatin is administered at a dose of about 50 to 70 mg/m² IV per cycle once every 3 to 4 weeks. In certain embodiments, cisplatin is administered at a dose of about 75 to 100 mg/m² IV per cycle once every 4 weeks.

Combination of SNS-595 and Carboplatin

In one embodiment, the second agent is carboplatin and the dose of carboplatin is about 50 mg/m² to about 400 mg/m², about 100 mg/m² to about 360 mg/m², about 150 mg/m² to 360 mg/m², about 200 mg/m² to 360 mg/m², about 250 mg/m² to 360 mg/m² or about 300 mg/m² to 360 mg/m². In another embodiment, the dose of carboplatin is about 300 mg/m². In another embodiment, the dose of carboplatin is about 360 mg/m². In certain embodiments, carboplatin can be administered continuously, by bolus injection, or by divided bolus injections over a particular time period such as, for example, one day.

In some embodiments, the methods of treating cancer comprise administering from about 1 m g/m² to about 150 mg/m² of SNS-595 and about 300 mg/m² of carboplatin. In certain embodiments, the methods comprise administering about 10 mg/m² SNS-595 and about 300 mg/m² of carboplatin; about 15 mg/m² SNS-595 and about 300 mg/m² of carboplatin; about 18 mg/m² SNS-595 and about 300 mg/m² of carboplatin; about 48 mg/m² SNS-595 and about 300 mg/m² of carboplatin; about 60 mg/m² SNS-595 and about 300 mg/m² of carboplatin; about 75 mg/m² SNS-595 and about 300 mg/m² of carboplatin; or about 90 mg/m² SNS-595 and about 300 mg/m² of carboplatin.

In some embodiments, the methods of treating cancer comprise administering from about 1 mg/m² to about 150 mg/m² of SNS-595 and about 360 mg/m² of carboplatin. In certain embodiments, the methods comprise administering about 10 mg/m² SNS-595 and about 360 mg/m² of carboplatin; 15 mg/m² SNS-595 and abut 360 mg/m² of carboplatin; 18 mg/m² SNS-595 and about 360 mg/m² of carboplatin; about 48 mg/m² SNS-595 and about 360 mg/m² of carboplatin; about 60 mg/m² SNS-595 and about 360 mg/m² of carboplatin; about 75 mg/m² SNS-595 and about 360 mg/m² of carboplatin; or about 90 mg/m² SNS-595 and about 360 mg/m² of carboplatin.

In certain embodiments, the methods of treating, preventing or managing a cancer comprise administering a total dosage of about 10 m g/m²-120 mg/m² SNS-595, in one embodiment, about 10-80 mg/m² SNS-595 in combination with a continuous intravenous dose of about 300 mg/m² of carboplatin once every 4 weeks. In certain embodiments, the methods of treating, preventing or managing a cancer comprise administering a total dosage of about 10 mg/m²-120 mg/m² SNS-595, in one embodiment, about 10-80 mg/m² SNS-595 in combination with a continuous intravenous dose of about 360 mg/m² of carboplatin once every 4 weeks, wherein the 4 week period comprises a treatment cycle. In some embodiments, the treatment cycle is repeated at least once. In some embodiments, the treatment cycle is repeated at least twice. In some embodiments, the treatment cycle is repeated at least three times. In some embodiments, the treatment cycle is repeated at least four times. In some embodiments, the treatment cycle is repeated at least six times.

Combination of SNS-595 and Gemcitabine

In one embodiment, the second agent is gemcitabine and the dose of gemcitabine is about 100 m g/m² to about 1500 mg/m², about 500 mg/m² to about 1500 mg/m², about 1000 mg/m² to about 1500 mg/m², about 1000 mg/m² to about 1400 mg/m² and about 1000 to about 1250 mg/m². In another embodiment, the dose of gemcitabine is about 1000 mg/m². In another embodiment, the dose of gemcitabine is about 1250 mg/m². In certain embodiments, gemcitabine can be administered continuously, by bolus injection, or by divided bolus injections over a particular time period such as, for example, one day.

In some embodiments, the methods of treating cancer comprise administering from about 1 mg/m² to about 150 mg/m² of SNS-595 and about 100 mg/m² to about 1500 mg/m² of gemcitabine. In certain embodiments, the methods comprise administering about 10 mg/m² SNS-595 and about 1000 mg/m² of gemcitabine; about 15 mg/m² SNS-595 and about 1000 mg/m² of gemcitabine; about 18 mg/m² SNS-595 and about 1000 mg/m² of gemcitabine; about 48 mg/m² SNS-595 and about 1000 mg/m² of gemcitabine; about 60 mg/m² SNS-595 and about 1000 mg/m² of gemcitabine; about 70 mg/m² SNS-595 and about 1000 mg/m² of gemcitabine; about 75 mg/m² SNS-595 and about 1000 mg/m² of gemcitabine; about 80 mg/m² SNS-595 and about 1000 mg/m² of gemcitabine; about 90 mg/m² SNS-595 and about 1000 mg/m² of gemcitabine; about 100 mg/m² SNS-595 and about 1000 mg/m² of gemcitabine.

In certain embodiments, the methods comprise administering about 10 mg/m² SNS-595 and about 1250 mg/m² of gemcitabine; about 15 mg/m² SNS-595 and about 1250 mg/m² of gemcitabine; about 18 mg/m² SNS-595 and about 1250 mg/m² of gemcitabine; about 48 mg/m² SNS-595 and about 1250 mg/m² of gemcitabine; about 60 mg/m² SNS-595 and about 1250 mg/m² of gemcitabine; about 70 mg/m² SNS-595 and about 1250 mg/m² of gemcitabine; about 75 mg/m² SNS-595 and about 1250 mg/m² of gemcitabine; 80 mg/m² SNS-595 and 1250 mg/m² of gemcitabine; 90 mg/m² SNS-595 and about 1250 mg/m² of gemcitabine; about 90 mg/m² SNS-595 and about 1250 mg/m² of gemcitabine.

In certain embodiments, the methods of treating, preventing or managing a cancer comprises administering a total dosage of about 10 mg/m²-100 mg/m² SNS-595, in one embodiment, about 10-80 mg/m² in combination with a continuous intravenous dose of about 1000 mg/m² or 1250 mg/m² of gemcitabine once a week for upto 7 weeks. In some embodiments, the method comprises administering a total dosage of about 20 mg/m²-60 mg/m² SNS-595 in combination with a continuous intravenous dose of about 1000 or 1250 mg/m² gemcitabine once a week for up to 4 weeks.

Duration (interval) between repeated administrations of the schedules can range from about 1 week to 8 weeks after the end of the schedule. In another embodiment, the interval is from 3 weeks to 6 weeks.

5.6.2 Exemplary Dosing Schedules of SNS-595 and Second Agents

In the embodiments of the present invention, SNS-595 and the second agents provided herein can be administered according to any schedule deemed suitable by a practitioner of skill in the art. Provided in this section are exemplary dosing schedules of SNS-595 in combination with the second agents that can be practiced in the methods provided herein.

In certain embodiments, SNS-595 and/or a pharmaceutically acceptable salt, solvate or hydrate thereof and the second agents are administered in cycles. In certain embodiments, SNS-595 and the second agents are administered in at least one cycle. In certain embodiments, SNS-595 and the second agents are administered in at least two cycles. In certain embodiments, SNS-595 and the second agents are administered in at least three cycles. In certain embodiments, SNS-595 and the second agents are administered in at least four cycles. In certain embodiments each cycle is at least 28 days. In one embodiment, the second agent is cisplatin. In one embodiment, the second agent is carboplatin. In one embodiment, the second agent is gemcitabine.

In certain embodiments, as discussed above, the initial dose of SNS-595 is administered before the administration of the second agent. In certain embodiments, the initial dose of SNS-595 is administered immediately before the administration of the second agent. In certain embodiments, administration of the second agent is initiated 1, 2, 3, 4, 8, 12, 16, 24, or 32 hours following administration of SNS-595, for instance, 1, 2, 3, 4, 8, 12, 16, 24, or 32 hours following completion of the administration of SNS-595.

6. EXAMPLES

Certain embodiments of the invention are illustrated by the following non-limiting example.

Example 1

Pharmaceutical Composition Suitable for Injection or Intravenous Infusion

Acidic compositions (<pH 4) provided the appropriate balance of increased solubility of SNS-595 and desirable pharmaceutical properties (e.g. increased patient comfort by causing less irritation at the delivery site). An illustrative example of a suitable composition comprises: 10 mg SNS-595 per mL of aqueous solution of 4.5% sorbitol that is adjusted to pH 2.5 with methanesulfonic acid. One protocol for making such a solution includes the following for making a 100 mg/10 mL presentation: 100 mg of SNS-595 and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.

Example 2

SNS-595 in Combination with Cisplatin

The effect of co-administration of SNS-595 and cisplatin was observed on the growth of ovarian carcinoma studied in athymic nude mice bearing subcutaneous A2780 xenografts. The mice were treated with SNS-595, cisplatin or the two in combination as indicated below.

TABLE 1

| Group | N | Compound | Dose (mg/kg) | Route | Schedule | Compound | Dose (mg/kg) | Route | Schedule |
|---|---|---|---|---|---|---|---|---|---|
| 1 | 10 | Vehicle | 0 | IV | qw x3 | Vehicle | 0 | IP | qw x3 |
| 2 | 10 | SNS-595 | 10 | IV | qw x3 | | | | |
| 3 | 10 | Cisplatin | 5 | IP | qw x3 | | | | |
| 4 | 10 | SNS-595 | 10 | IV | qw x3 | Cisplatin | 5 | IP | qw x3 |

Animal treatment was initiated when mean tumor volume was 200 mm$^3$. The combination was co-dosed once a week for three weeks. Tumor volumes and animal body weight were measured twice weekly. The data for body weight loss, % tumor growth inhibition and tumor growth delays in the animals is shown in Table 2.

TABLE 2

| Group | BW Nadir (Day of) | % Tumor Growth Inhibition (Day 11) | Tumor Growth Delay (days) |
|---|---|---|---|
| SNS-595 10 mg/kg qw x 3 | −4.7% (Day 4) | 21.7% (p > 0.05) | 5.5 |
| Cisplatin 5 mg/kg qw x 3 | −10.9% (Day 11) | 49.0% (p < 0.05) | 11.0 |
| Combination | −14.1% (Day 11) | 64.2% (p < 0.05) | 14.0 |

Animals treated with SNS-595 alone (10 mg/kg qw x3) had a tumor growth inhibition of 21.7% while those treated with cisplatin alone (5 mg/kg qw x3) had 49% tumor growth inhibition. When SNS-595 (10 mg/kg qw x3) was combined with cisplatin (5 mg/kg qw x3) the tumor growth inhibition increased to 64.2%. Animals treated with the combination had a mean body weight loss of 14% with the nadir occurring on day 11. The effect of the treatment on the tumor volume, % body weight change and % survival is provided in FIGS. 1, 2 and 3, respectively. The survival of the mice treated with the combination of SNS-595 and cisplatin was increased compared to the vehicle or either single agent.

Example 3

SNS-595 in Combination with Carboplatin

The effect of co-administration of SNS-595 and carboplatin was observed on the growth of non-small cell lung carcinoma, athymic nude mice bearing subcutaneous H460. The mice were treated with SNS-595, carboplatin or the two in combination as indicated below.

TABLE 3

| Group | N | Compound | Dose (mg/kg) | Route | Schedule | Compound | Dose (mg/kg) | Route | Schedule |
|---|---|---|---|---|---|---|---|---|---|
| 1 | 10 | Untreated | | | | | | | |
| 2 | 10 | SNS-595 | 10 | IV | qw x5 | | | | |
| 3 | 10 | Carboplatin | 75 | IP | qw x3 | | | | |
| 4 | 10 | SNS-595 | 10 | IV | qw x5 | Carboplatin | 75 | IP | qw x3 |

Animal treatment was initiated when mean tumor volume was 200 mm$^3$. The combination was co-dosed once a week for three weeks. Tumor volumes and animal body weight were measured twice weekly. The data for body weight loss, % tumor growth inhibition and tumor growth delays in the animals is shown in Table 4.

TABLE 4

| Group | BW Nadir (Day of) | % Tumor Growth Inhibition (Day 16) | Tumor Growth Delay (days) |
|---|---|---|---|
| SNS-595 10 mg/kg qw x 5 | −0.7% (Day 4) | 53.2% (p > 0.05) | 23.0 |
| Carboplatin 75 mg/kg qw x 3 | −2.8% (Day 16) | 31.6% (p > 0.05) | 12.5 |
| Combination | −7.9% (Day 20) | 74.6% (p < 0.05) | 23.0 |

Animals treated with SNS-595 alone (10 mg/kg qw x5) had a tumor growth inhibition of 53% while those treated with carboplatin alone (75 mg/kg qw x3) had 32% tumor growth inhibition. When SNS-595 (10 mg/kg qw x5) was combined with carboplatin (75 mg/kg qw x3) the tumor growth inhibition increased to 75%. Animals treated with the combination had a mean body weight loss of 8%. This weight loss was recoverable and acceptable for the combination treatment. The effect of the treatment on the tumor volume, % body weight change and % survival is provided in FIGS. 5, 6 and 7, respectively. The survival of mice treated with the combination of SNS-595 and carboplatin was increased compared to those treated with carboplatin alone.

Example 4

SNS-595 in Combination with Gemcitabine

The effect of co-administration of SNS-595 and gemcitabine on the growth of non-small cell lung carcinoma, athymic nude mice bearing subcutaneous H460 xenografts were treated with SNS-595, gemcitabine or the two in combination as indicated below.

TABLE 5

| Group | N | Compound | Dose (mg/kg) | Route | Schedule | Compound | Dose (mg/kg) | Route | Schedule |
|---|---|---|---|---|---|---|---|---|---|
| 1 | 10 | Vehicle | 0 | IV | qw x3 | Vehicle | 0 | IP | biw x2 24 h post IV |
| 2 | 10 | SNS-595 | 10 | IV | qw x3 | | | | |
| 3 | 10 | Gemcitabine | 75 | IP | biw x2 | | | | |
| 4 | 10 | SNS-595 | 10 | IV | qw x3 | Gemcitabine | 75 | IP | biw x2 |

Animal treatment was initiated when mean tumor volume was greater than 200 mm$^3$. SNS-595 was administered once a week and gemcitabine was twice weekly as indicated above with the combination being co-dosed. In the vehicle group, the gemcitabine vehicle was administered 24 hours after the SNS-595 vehicle representing additional treatment arms in the experiment. Tumor volume and animal body weight was measured at least twice weekly. The data for body weight loss, % tumor growth inhibition and tumor growth delays in the animals is shown in Table 6.

TABLE 6

| Group | BW Nadir (Day of) | % Tumor Growth Inhibition (Day 11) | Tumor Growth Delay (days) |
|---|---|---|---|
| SNS-595 10 mg/kg qw x 3 | −5.9% (Day 11) | 61.9% (p < 0.05) | 11.0 |
| Gemcitabine 75 mg/kg Biw x 2 | −7.4% (Day 11) | 36.6% (p > 0.05) | 5.0 |
| Combination | −7.9% (Day 18) | 81.7% (p < 0.01) | 51.0 |

Animals treated with SNS-595 alone (10 mg/kg qw x3) had a tumor growth inhibition of 62% while those treated with gemcitabine alone (75 mg/kg biw x2) had 37% tumor growth inhibition. When SNS-595 (10 mg/kg qw x3) was combined with gemcitabine (75 mg/kg biw x2) the tumor growth inhibition increased to 82%. Animals treated with the combination had a mean body weight loss of 8% with the nadir occurring on day 24. This weight loss was recoverable and acceptable for the combination treatment. The effect of the treatment on the tumor volume, % body weight change and % survival is provided in FIGS. 7, 8 and 9, respectively. The survival of mice treated with the combination of SNS-595 and gemcitabine was increased compared to the vehicle or either single agent.

Example 5

SNS-595 in Combination with Gemcitabine

The effect of co-administration of SNS-595 and gemcitabine on the growth of pancreatic carcinoma, NIH-III mice bearing subcutaneous BxPC-3 xenografts were were treated with SNS-595, gemcitabine or the two in combination as follows.

TABLE 7

| Group | N | Compound | Dose (mg/kg) | Route | Schedule | Compound | Dose (mg/kg) | Route | Schedule |
|---|---|---|---|---|---|---|---|---|---|
| 1 | 10 | Vehicle | 0 | IV | qw x3 | Vehicle | 0 | IP | biw x3 |
| 2 | 10 | SNS-595 | 15 | IV | qw x3 | | | | |
| 3 | 10 | Gemcitabine | 65 | IP | biw x3 | | | | |
| 4 | 10 | SNS-595 | 15 | IV | qw x3 | Gemcitabine | 65 | IP | biw x3 |

Animal treatment was initiated when mean tumor volume was greater than 250 mm$^3$. SNS-595 was administered once a week and gemcitabine was twice weekly for two weeks followed by one additional dose as indicated above with the combination being co-dosed. Tumor volume and animal body weight was measured at least once weekly. SNS-595 was administered once a week and gemcitabine was twice weekly for two weeks followed by one additional dose as indicated above with the combination being co-dosed. Tumor volume and animal body weight was measured at least once weekly. The data for body weight loss, % tumor growth inhibition and tumor growth delays in the animals is shown in Table 8.

TABLE 8

| Group | BW Nadir (Day of) | % Tumor Growth Inhibition (Day 38) | Tumor Growth Delay (days) |
|---|---|---|---|
| SNS-595 15 mg/kg qw x 3 | −2.5% (Day 11) | 25.9% (p > 0.05) | 23.0 |
| Gemcitabine | 0% | 20.2% | 12.5 |

TABLE 8-continued

| Group | BW Nadir (Day of) | % Tumor Growth Inhibition (Day 38) | Tumor Growth Delay (days) |
|---|---|---|---|
| 65 mg/kg biw x 2 | (Day 0) | (p > 0.05) | |
| Combination | −9.9% (Day 21) | 71.6% (p < 0.01) | x |

Animals treated with SNS-595 alone (15 mg/kg qw ×3) had a tumor growth inhibition of 26% while those treated with gemcitabine alone (65 mg/kg biw ×3) had 20% tumor growth inhibition. When SNS-595 (15 mg/kg qw ×3) was combined with gemcitabine (65 mg/kg biw ×3) the tumor growth inhibition increased to 72%. Animals treated with the combination had a mean body weight loss of 10% with the nadir occurring on day 21 of treatment. This weight loss was recoverable and acceptable for the combination treatment. The effect of the treatment on the tumor volume, % body weight change and % survival is provided in FIGS. 10, 11 and 12, respectively. The survival of mice treated with the combination of SNS-595 and gemcitabine was increased compared to the vehicle or either single agent.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating non-small cell lung cancer comprising administering a patient in need thereof a dose of about 1 mg/m² to about 150 mg/m² of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof and a dose of about 100 mg/m² to about 1500 mg/m² gemcitabine.

2. The method of claim 1, wherein the dose of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof is from about 10 mg/m² to about 90 mg/m².

3. The method of claim 1, wherein the dose of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof is about 18 mg/m².

4. The method of claim 1, wherein the dose of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof is about 48 mg/m².

5. The method of claim 1, wherein the dose of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof is about 60 mg/m².

6. The method of claim 1, wherein the dose of (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof is about 75 mg/m².

7. The method of claim 1, wherein the dose of gemcitabine is from about 1000 mg/m² to about 1500 mg/m².

8. The method of claim 1, wherein the dose of gemcitabine is about 1000 mg/m² once a week.

9. The method of claim 1, wherein the dose of gemcitabine is about 1250 mg/m² once a week.

10. The method of claim 1, wherein the cancer is relapsed, refractory or resistant to conventional therapy.

11. The method of claim 1, further comprising administering a therapeutically effective amount of another active agent or a support care therapy.

12. The method of claim 11, wherein the active agent is a therapeutic antibody that specifically binds to a cancer antigen, hematopoietic growth factor, cytokine, anti-cancer agent, antibiotic, cox-2 inhibitor, immunomodulatory agent, immunosuppressive agent or a corticosteroid.

13. The method of claim 1, wherein (+)-1,4-dihydro-7-[(3S, 4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof is administered once a week for three weeks.

14. The method of claim 1, wherein (+)-1,4-dihydro-7-[(3S, 4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof administered once every three weeks.

15. The method of claim 1, wherein (+)-1,4-dihydro-7-[(3S, 4S)-3-methoxy-4-(methylamino)-1-pyrrolidinyl]-4-oxo-1-(2-thiazolyl)-1,8-naphthyridine-3-carboxylic acid and/or a pharmaceutically acceptable salt or hydrate thereof thereof is administered as an IV injection.

* * * * *

UNITED STATES PATENT AND TRADEMARK OFFICE
CERTIFICATE OF CORRECTION

PATENT NO. : 8,518,872 B2  Page 1 of 1
APPLICATION NO. : 12/739139
DATED : August 27, 2013
INVENTOR(S) : Jeffrey A. Silverman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 119 days.

Signed and Sealed this

Fifteenth Day of September, 2015

Michelle K. Lee
*Director of the United States Patent and Trademark Office*